(12) United States Patent
Blodgett

(10) Patent No.: US 10,900,987 B2
(45) Date of Patent: Jan. 26, 2021

(54) ROBUST PARTICLE VELOCITY MEASUREMENT

(71) Applicant: The Johns Hopkins University, Baltimore, MD (US)

(72) Inventor: David W. Blodgett, Ellicott City, MD (US)

(73) Assignee: The Johns Hopkins University, Baltimore, MD (US)

( * ) Notice: Subject to any disclaimer, the term of this patent is extended or adjusted under 35 U.S.C. 154(b) by 603 days.

(21) Appl. No.: 15/347,176

(22) Filed: Nov. 9, 2016

(65) Prior Publication Data
US 2017/0131320 A1    May 11, 2017

Related U.S. Application Data

(60) Provisional application No. 62/253,242, filed on Nov. 10, 2015.

(51) Int. Cl.
| | |
|---|---|
| *G01P 3/36* | (2006.01) |
| *A61B 5/00* | (2006.01) |
| *G01P 5/26* | (2006.01) |
| *A61B 5/026* | (2006.01) |

(52) U.S. Cl.
CPC .............. *G01P 3/36* (2013.01); *A61B 5/4064* (2013.01); *G01P 5/26* (2013.01); *A61B 5/0261* (2013.01)

(58) Field of Classification Search
None
See application file for complete search history.

(56) References Cited

U.S. PATENT DOCUMENTS

| | | | | |
|---|---|---|---|---|
| 3,753,616 A | * | 8/1973 | Goethert | G01P 5/26 356/28 |
| 3,866,055 A | * | 2/1975 | Pike | G01P 5/26 250/564 |
| 3,915,572 A | * | 10/1975 | Orloff | G01P 5/26 356/28 |
| 4,387,993 A | * | 6/1983 | Adrian | G01N 15/0205 356/28 |
| 4,537,507 A | * | 8/1985 | Hess | G01N 15/0205 356/28.5 |
| 4,986,659 A | * | 1/1991 | Bachalo | G01N 15/0205 356/336 |
| 5,070,483 A | * | 12/1991 | Berni | G01H 9/00 356/28.5 |
| 5,148,229 A | * | 9/1992 | Wiseall | G01P 5/20 356/28 |
| 6,064,473 A | * | 5/2000 | Hironaga | G01N 15/0205 356/28.5 |
| 6,424,407 B1 | * | 7/2002 | Kinrot | G01D 5/347 345/166 |
| 9,684,076 B1 | * | 6/2017 | Feldkhun | G01S 17/89 |
| 2003/0020920 A1 | * | 1/2003 | Dave | G01N 21/4795 356/479 |

(Continued)

*Primary Examiner* — Hovhannes Baghdasaryan
(74) *Attorney, Agent, or Firm* — Sung T. Kim

(57) ABSTRACT

A method for particle velocity measurement may include transmitting an optical beam from an optical source, splitting the optical beam into a first beam and a second beam where the first beam and the second beam each have different polarizations, directing the first beam and the second beam toward an object, and determining a velocity of the object based on receiving the first and second beams reflected from the object.

18 Claims, 7 Drawing Sheets

(56) References Cited

U.S. PATENT DOCUMENTS

2009/0046296 A1* 2/2009 Kilpatrick .............. G01H 9/004
                356/484
2009/0147267 A1* 6/2009 Lawall ................... G01H 9/004
                356/502

* cited by examiner

ROBUST PARTICLE VELOCITY MEASUREMENT

CROSS-REFERENCE TO RELATED APPLICATIONS

This application claims the benefit of U.S. Provisional Application No. 62/253,242 filed on Nov. 10, 2015, the entire contents of which are hereby incorporated herein by reference.

TECHNICAL FIELD

Exemplary embodiments of the present disclosure generally relate to particle velocity measurement techniques, and more specifically relate to overlapping (or nearly overlapping) coherent optical beams in an optical detector that can measure velocity of particles in a liquid or gas.

BACKGROUND

Particle velocity measurement in a gas or liquid may be performed using a conventional structure for embodying a laser Doppler velocimeter (LDV). A conventional structure for LDV employs two overlapping, coherent optical beams to form a measurement volume at their intersection as shown in FIG. 1A. In this regard, a first beam 100 and a second beam 110 overlap at an overlap volume 120. Within the overlap volume 120, a linear fringe field is established, with the frequency (spatial separation) of the fringes being dictated by the incidence angle between the first and second beams 100 and 110. As a particle 130 propagates through the fringe field, the particle 130 passes through regions of high and low optical intensity. A simple optical detector 140 can measure the fluctuations associated with passage of the particle 130 through the high and low optical intensity regions, and a result measured by the detector appears as a sinusoid 150, with the frequency of the sinusoid 150 dictated by the particle velocity (V) of the particle 130.

The measurement process described in reference to FIG. 1A can suffer from inaccuracies in some cases. For example, as shown in FIG. 1B, any error in overlap angle or the presence of any microstructure inhomogeneities 160 (e.g., associated with turbulent environments where there may be spatially varying refractive indices) may result in non-uniform fringes that may then distort the measured response (i.e., the frequency of the measured sinusoid 170 is now a function of both the fringe spacing and the particle velocity (V)).

BRIEF SUMMARY OF SOME EXAMPLES

In one example embodiment, a particle velocity measurement system is provided. The particle velocity measurement system may include an optical source configured to generate an optical beam, a beam splitter configured to split the optical beam into a first beam and a second beam where the first beam and the second beam each have different polarizations, a combiner to direct the first and second beams toward an object and a detector configured to receive the first beam and the second beam reflected from the object to determine a velocity of the object.

In another example embodiment, a method for particle velocity measurement is provided. The method may include transmitting an optical beam from an optical source, splitting the optical beam into a first beam and a second beam with the first beam and the second beam each having different polarizations, directing the first beam and the second beam toward an object, and determining a velocity of the object based on receiving the first and second beams reflected from the object.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

DETAILED DESCRIPTION

Figure 1A:
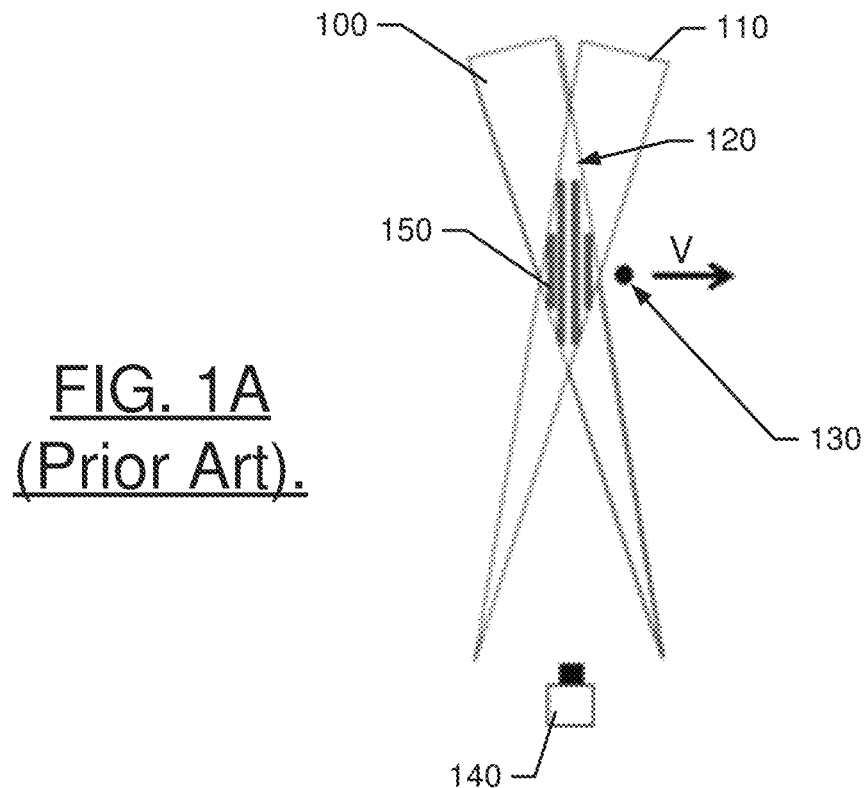
FIG. 1A illustrates a conceptual diagram showing one example of a conventional particle velocity measurement system.
Figure 1B:
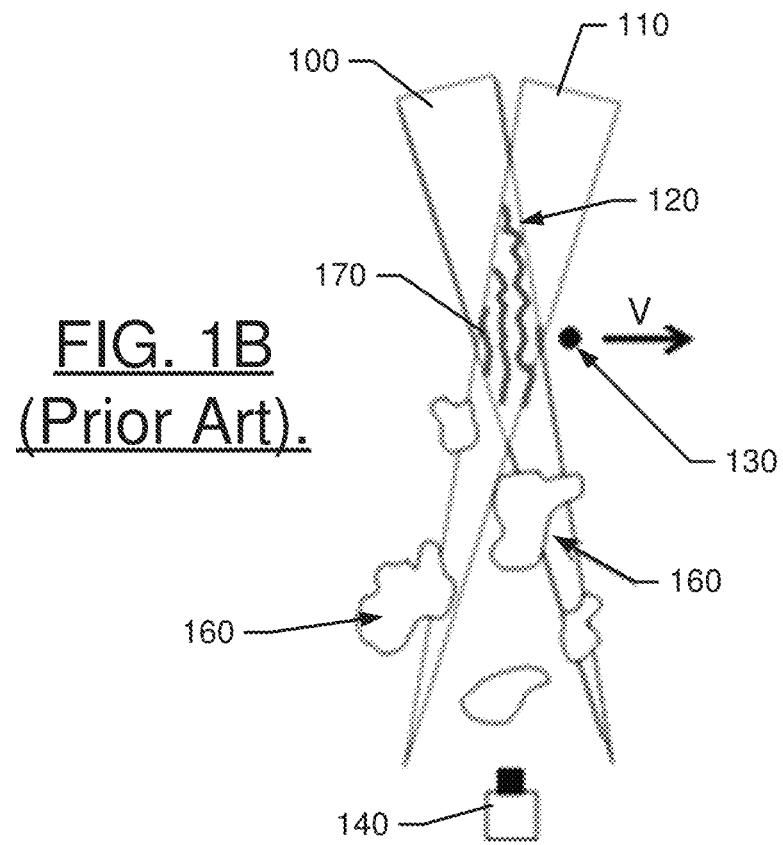
FIG. 1B illustrates the system of FIG. 1A operating in an environment with microstructure inhomogeneity.

Some example embodiments now will be described more fully hereinafter with reference to the accompanying drawings, in which some, but not all example embodiments are shown. Indeed, the examples described and pictured herein should not be construed as being limiting as to the scope, applicability or configuration of the present disclosure. Rather, these example embodiments are provided so that this disclosure will satisfy applicable legal requirements. Like reference numerals refer to like elements throughout.

As used herein, the terms "component," "module," and the like are intended to include a computer-related entity, such as but not limited to hardware, software, firmware, or a combination thereof. For example, a component or module may be, but is not limited to being, a process running on a processor, a processor, an object, an executable, a thread of execution, and/or a computer. By way of example, both an application running on a computing device and/or the computing device can be a component or module. One or more components or modules can reside within a process and/or thread of execution and a component/module may be localized on one computer and/or distributed between two or more computers. In addition, these components can execute from various computer readable media having various data structures stored thereon. The components may communicate by way of local and/or remote processes such as in accordance with a signal having one or more data packets, such as data from one component/module interacting with another component/module in a local system, distributed system, and/or across a network such as the Internet with other systems by way of the signal. Each respective component/module may perform one or more functions that will be described in greater detail herein. However, it should be appreciated that although this example is described in terms of separate modules corresponding to various functions performed, some examples may not necessarily utilize modular architectures for employment of the respective different functions. Thus, for example, code may be shared between different modules, or the processing circuitry itself may be configured to perform all of the functions described as being associated with the components/modules described herein. Furthermore, in the context of this disclosure, the term "module" should not be understood as a nonce word to identify any generic means for performing functionalities of the respective modules. Instead, the term "module" should be understood to be a modular component that is specifically configured in, or can be operably coupled to, the processing circuitry to modify the behavior and/or capability of the processing circuitry based on the hardware and/or software that is added to or otherwise operably coupled to the processing circuitry to configure the processing circuitry accordingly.

Some example embodiments may enable the provision of a system capable of improving the accuracy of particle velocity measurements in turbulent environments. For example, some embodiments may provide beams that overlap (or nearly overlap) to ensure that only a small deviation in overlap will occur at the maximum velocity measurement range. The overlapping of the beams may help mitigate relative phase errors between beams and mitigate phase error noise. Thus, for example, good quality particle velocity measurement can be achieved even for relatively small velocities in turbid environments. Brain to computer interface (BCI) technology and other applications may therefore be improved by providing practically feasible sensors to be employed for real-time measurement of particle velocities, which may be indicative of neural activity.

As indicated above, some example embodiments may enable the provision of a mechanism by which to employ overlapping beams to enable the provision of a system capable of improving the accuracy of particle velocity measurements in turbulent environments. Of note, although the contents of this disclosure will refer to beams as overlapping, it should be appreciated that some small deviation in overlap should still be considered as overlapping for purposes of construing the examples provided herein. In this regard, a small amount of deviation in overlap at the maximum velocity measurement range can be tolerated, and still produces relatively good results. As discussed above, the overlapping of the beams can mitigate relative phase errors between beams and also mitigates phase error noise to enable good quality particle velocity measurement to be achieved even for relatively small velocities such as those experienced in measuring neural signatures.

Figure 2:
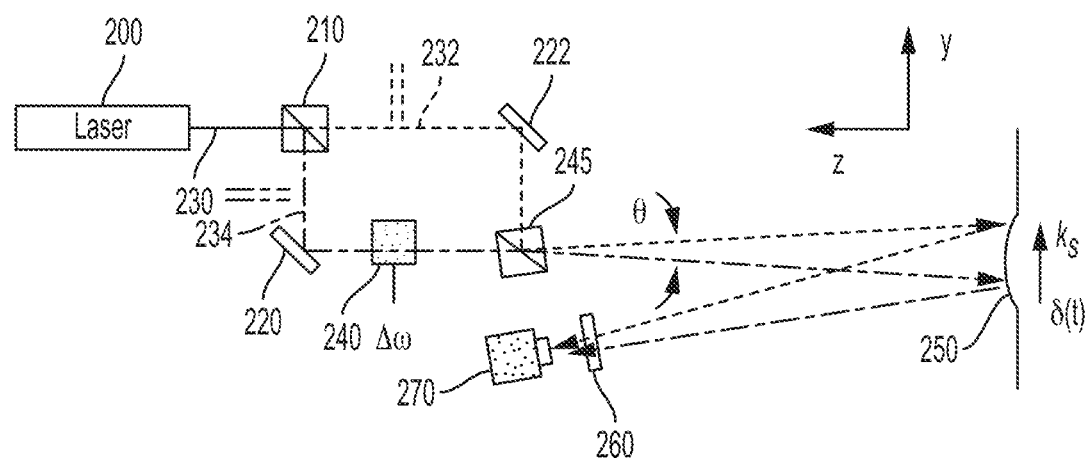
FIG. 2 illustrates a concept view of a particle velocity measurement system of an example embodiment.

FIG. 2 illustrates a conceptual diagram of a system for providing velocity measurement according to an example embodiment. As shown in FIG. 2, the system may include a laser 200, a beam splitter 210, a first mirror 220, and a second mirror 222. The laser 200 may be a short coherence length laser capable of operating in continuous and/or pulsed operating modes. The laser 200 may generate a beam 230 that is transmitted to the beam splitter 210, where the beam 230 is split into a first beam 232 and a second beam 234. The first and second beams 232 and 234 may be cross polarized. In other words, the first beam 232 may have a polarization (e.g., horizontal) that is orthogonal to the polarization of the second beam 234 (e.g., vertical). Although not required, some embodiments may provide one of the beams (in this case the second beam 234) through a frequency shifter 240. Thereafter, the first and second beams 232 and 234 may be substantially overlapped with each other (e.g., having at most a small angle of deviation therebetween) responsive to passing through a combiner 245. Thus, for example, the first and second beams 232 and 234 may substantially traverse the same path. However, in some cases, the combiner 245 may put a relatively small angle ($\theta$) of separation between the first and second beams 232 and 234 as they approach a surface displacement 250 (e.g., a medium having an object, such as one or more particles, therein whose velocity is to be measured). Beams reflected from the surface displacement 250, corresponding to the first and second beams 232 and 234, may then pass through a polarizer 260 (e.g., a 45 degree polarizer) to be received by a detector 270, where the reflected cross-polarized beams (e.g., 232 and 234) may be coherently mixed.

Velocity measurements of the object can then be made based on the reflected beams received by the detector 270. For example, the measure of velocity may correspond to the phase change between the reflected beams that are received by the detector 270. This phase change may be seen as a frequency shift in the laser and is due to the Doppler shift from the object, or surface displacement 250. In this regard, for small angular separations, there is still substantial overlap between the beams for a certain distance. In the example of FIG. 2, the first and second beams 232 and 234 overlap at the transmission side (e.g., before entering the medium) and have only a small angle deviation between them. Thus, for example, the first and second beams 232 and 234 may be largely overlapping at the maximum velocity measurement range (i.e., the maximum range at which velocity measurements are made). If the object being measured (e.g., a particle) moves, a Doppler shift is detected in the reflected light. The Doppler shift determines whether the movement was up/down or left/right from the detector (i.e., in-plane motion) and is indicative of directional information related to the velocity measurement that is made based on the phase change. A potential advantage of this approach is that the near common-path design, which is provided by the substantially overlapping beam arrangement, helps mitigate relative phase errors between the two beams along the propagation distance.

Figure 3:
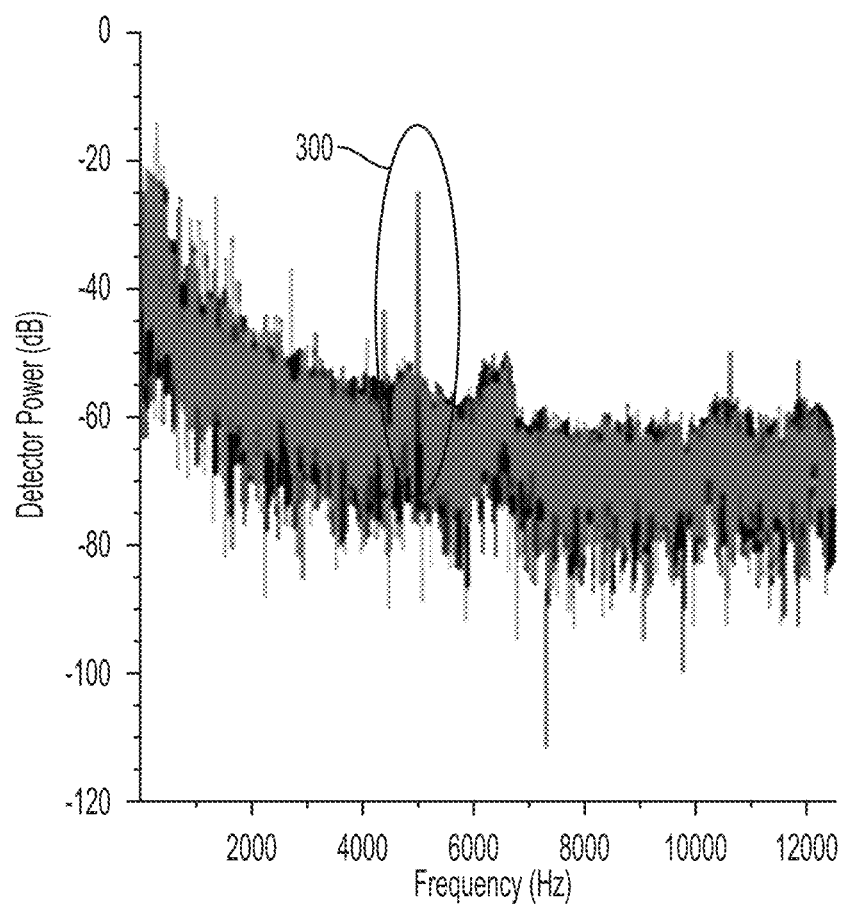
FIG. 3 illustrates a plot of measured results from a vibrating target operating at 5 kHz according to an example embodiment.

FIG. 3 illustrates the validity of the embodiments discussed above with respect to FIG. 2. For example, the plot depicted in FIG. 3 shows measured velocity from a piezoelectric (PZT) actuator operating at 5 kHz that is vibrating a piece of spectralon (e.g., Lambertian reflecting material). As shown in FIG. 3, a power spike 300 is noted at 5 kHz, demonstrating the validity of this approach. The ability to mitigate phase error noise may be critical for the measurement of very small velocities.

Figure 4:
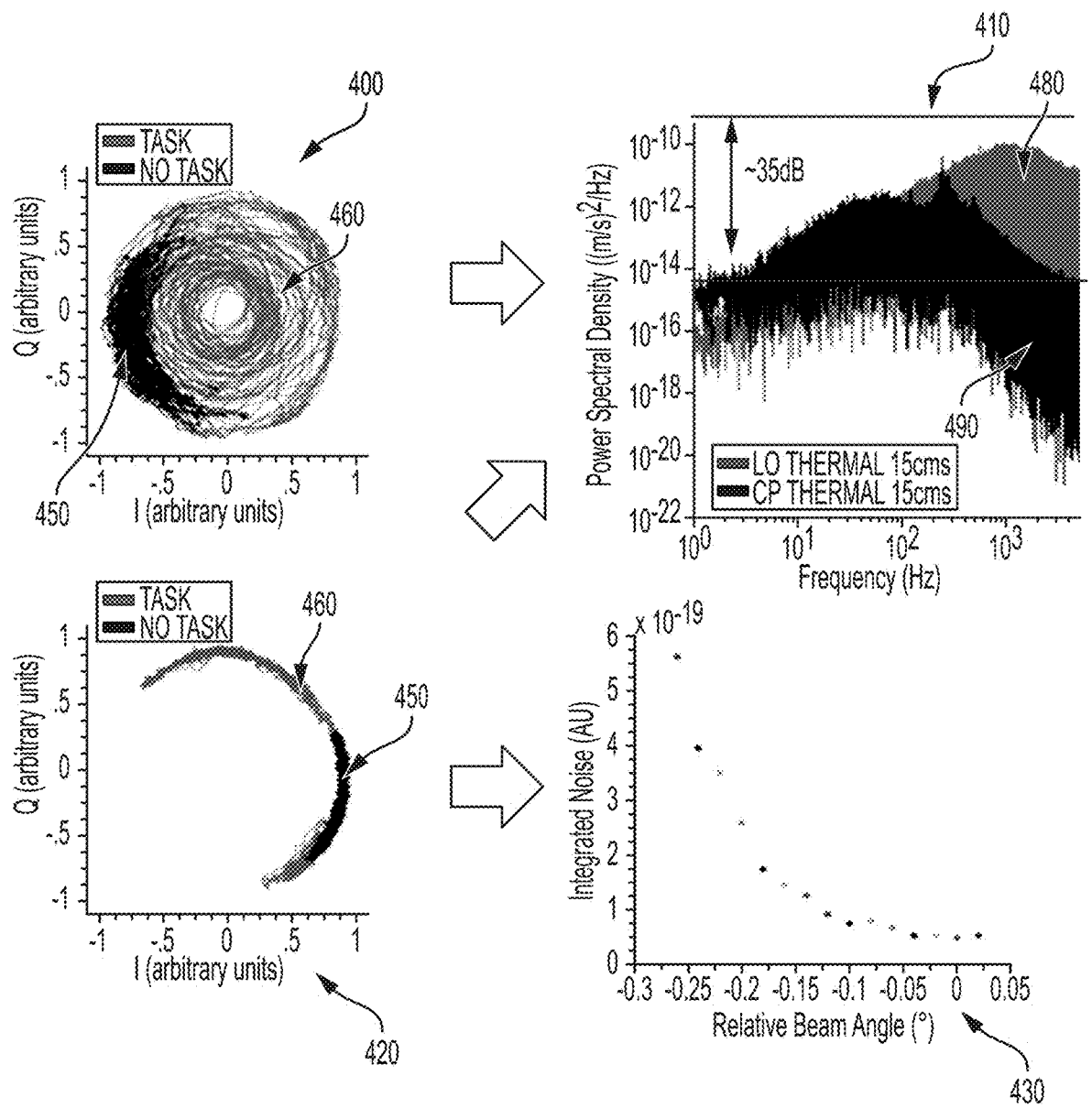
FIG. 4 illustrates a series of plots comparing a heterodyne system and a system of an example embodiment.

FIG. 4 illustrates various plots demonstrating phase noise reduction using example embodiments. In this regard, plot 400 shows an in-phase/quadrature plot for measured results showing relative performance of a conventional heterodyne system (out-of-plane velocity) and plot 420 illustrates measured results employing a system of an example embodiment. The data 450 is for operation in a pristine environment without any refractive noise. The data 450 shows that the magnitude of the velocity stays constant with drift largely due to mechanical vibrations in the two systems. The data 460 shows what happens to the phase error when refractive noise is introduced. Plot 410 is a plot of the power spectral density (PSD) for the heterodyne system (480) and an example embodiment (490) when operating in the presence of refractive noise. Plot 410 shows a maximum noise floor reduction of about 35 dB. Finally, plot 430 demonstrates the dependence of phase noise reduction as a function of beam separation angle demonstrating the benefit of example embodiments.

Example embodiments may provide a mechanism by which to make range-gated measurements using a pulsed laser based on a fringe pattern existing (if common polarizations are used) continuously along the beam propagation path. Range-gated measurements may be measurements taken at different ranges along the beams. Typically, these types of measurements are taken where the two beams cross. However, in present embodiments, the beams may cross over a very long range. If using a pulsed laser, velocities at different ranges may be differentiated by determining the velocities as a function of time. Additionally, the fringe pattern may occur where there is constructive and/or destructive interference.

In this regard, by employing a common, or near-common, path design, relative phase errors may be mitigated. Meanwhile, to the contrary, conventional LDV structures generally only overlap at one range. The position of the overlap region defines a measurement volume, and that measurement volume is essentially at a fixed range where the two beams overlap. Generally speaking, a small angular separation between the beams will help overcome refractive index noise. Example embodiments may also support the use of a high-power, short coherence length laser since the optical path lengths are balanced.

The concept of operation associated with example embodiments may be embodied in various structures that can be operated in multiple configurations. Cross polarizing of the beams (one of which will be an object beam and the other of which will be the reference beam) may provide various advantages. For example, cross-polarizing the object and reference beams may support the use of a frequency modulator in one of the arms to support frequency modulation (FM) demodulation schemes. Additionally or alternatively, cross-polarizing the object and reference beams may support the use of optical in-phase quadrature (IQ) demodulation schemes. This may remove the need for the frequency modulator and greatly simplify the transmitter design.

Figure 5:
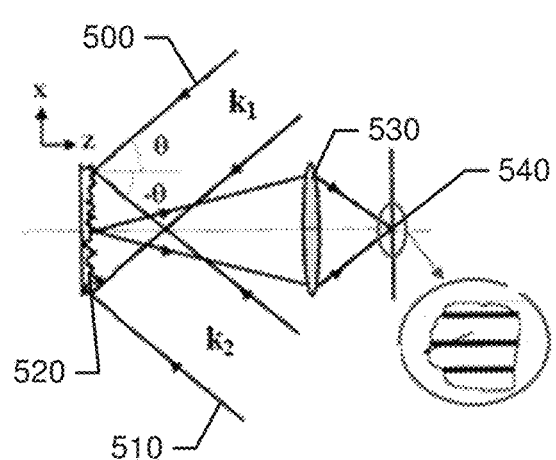
FIG. 5 illustrates a concept view of a non-overlapping beam illumination scheme of an example embodiment.

Some example embodiments may be modified from using two illumination beams with a small separation angle (as shown in FIG. 2) to using two overlapping beams with a split receiver. FIG. 5 illustrates an example of separate object beams 500 and reference beams 510 being provided in a non-overlapping fashion. After reflection of the object beam 500 and the reference beam 510 from the object (e.g., a particle in the human brain) 520 is measured, reflected waves from the reflected object beam 500 and the reflected reference beam 510 are passed through a lens 530 and focused at a focus point 540 for collection and measuring.

Figure 6:
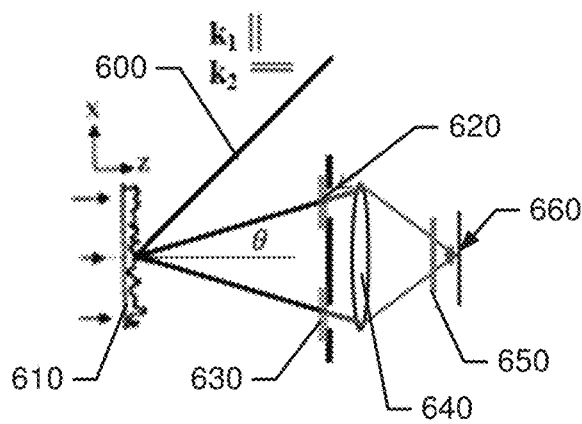
FIG. 6 illustrates a concept view of a common-path beam illumination scheme of an example embodiment.

To employ the concepts of an example embodiment, the structure of FIG. 6 may be employed. As shown in FIG. 6, a common path, overlapping beam 600, which includes both the reference beam and the object beam with orthogonal polarizations, encounters the object 610 being measured. Reflected waves from the overlapping beam 600 are then separated by a horizontal polarizer 620 and a vertical polarizer 630 to form polarized beams that pass through lens 640, which directs the polarized beams toward a focus point 660. The horizontal polarizer 620 and the vertical polarizer 630 may be provided in a component that effectively acts as a beam splitter, although it is possible that another conventional beam splitter may be included and be used to form the overlapping beam (e.g., similar to FIG. 2 except without the small angle formed between the beams). Another polarizer (e.g., a 45 degree polarizer) 650 may then be employed prior to the polarized beams converging at focus point 660. A potential advantage of this approach is that the two beams are completely overlapping during transmission through the medium to maximize phase error reduction. In this configuration, the two beams are still cross-polarized, which allows separation at the two apertures placed in front of the lens (e.g., the apertures at which the horizontal polarizer 620 and the vertical polarizer 630 are disposed). One aperture only passes the horizontally polarized light and the other the vertically polarized light. Optical mixing occurs by passing the horizontal/vertical polarized light through a polarizer rotated at 45 degrees, and the two beams will interfere at a detector (e.g., a photodetector positioned at the focus point 660).

Doppler shift may be detected based on movement of the object 610. The Doppler shift is scaled by the angle ($\theta$) between the two beams (e.g., the beams that pass through the horizontal polarizer 620 and the vertical polarizer 630) of FIG. 6. Therefore, if the object is moved either further away or closer to the lens, the Doppler shift will shift by a known amount. This known scaling then allows for the separation of velocity measurements at different distances. For example, in one embodiment, if the velocity of the object 610 is 100 m/s, then at a separation angle of 10 degrees the system may record a velocity of only 17.4 m/s. This apparent velocity will increase when the object 610 is closer to the lens 640. Therefore, assuming a known constant velocity for the object 610, the object range can be determined simply by looking at the measured apparent velocity. For example, at distances less than 15 mm (e.g., those found in BCI applications), the angular deviations will be quite large even for distance variations of only 1-2 mm. One can extend the approach described herein in relation to having a single detector by using an imaging array instead of the single detector (with frequency discrimination), or a linear array (with spatial separation). In an embodiment, a full imaging array would use information from both frequency discrimination and spatial separation to provide a 3D velocity image.

Figure 7:
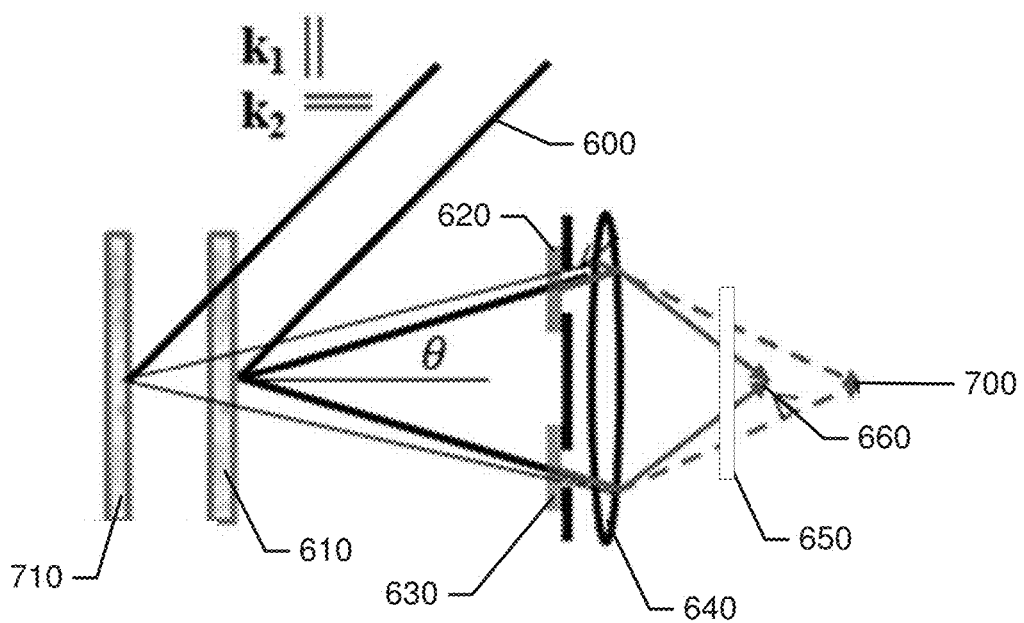
FIG. 7 illustrates a modification to allow detection of particle velocity at multiple depths in accordance with an example embodiment.

Given the principles discussed above, it can be appreciated that the object's distance from the lens 640 can be determined by the location of the focus point. In this regard, as shown in FIG. 7, a second focus point 700 is provided to correlate to a second object 710, which is located at a different distance (e.g., a deeper depth) than the object 610. As shown in FIG. 7, portions of the beam 600 reflect or scatter off of two different objects (e.g., object 610 and second object 710), resulting in two different focus points (e.g., focus point 660 and second focus point 700). Therefore, one can use different optical detectors (e.g., one at each focus point) to measure velocity at different depths. For BCI applications this would allow for range-resolved velocity measurements of blood flow, which correlates to neural activity as demonstrated by the use of Blood Oxygenation Level Detection (BOLD) techniques.

In an example embodiment, the medium in which particles or objects measured are located may be a brain (e.g., a human brain, primate brain, or other animal brain), or the head of an individual. The components described herein may therefore be provided in a sensor that can be worn on or positioned at the head, or even implanted into a portion of the head. The sensor can therefore detect neural activity or blood flow through the skull with relatively high accuracy, but also with relatively little structure, size, weight, and power requirements.

Figure 8:
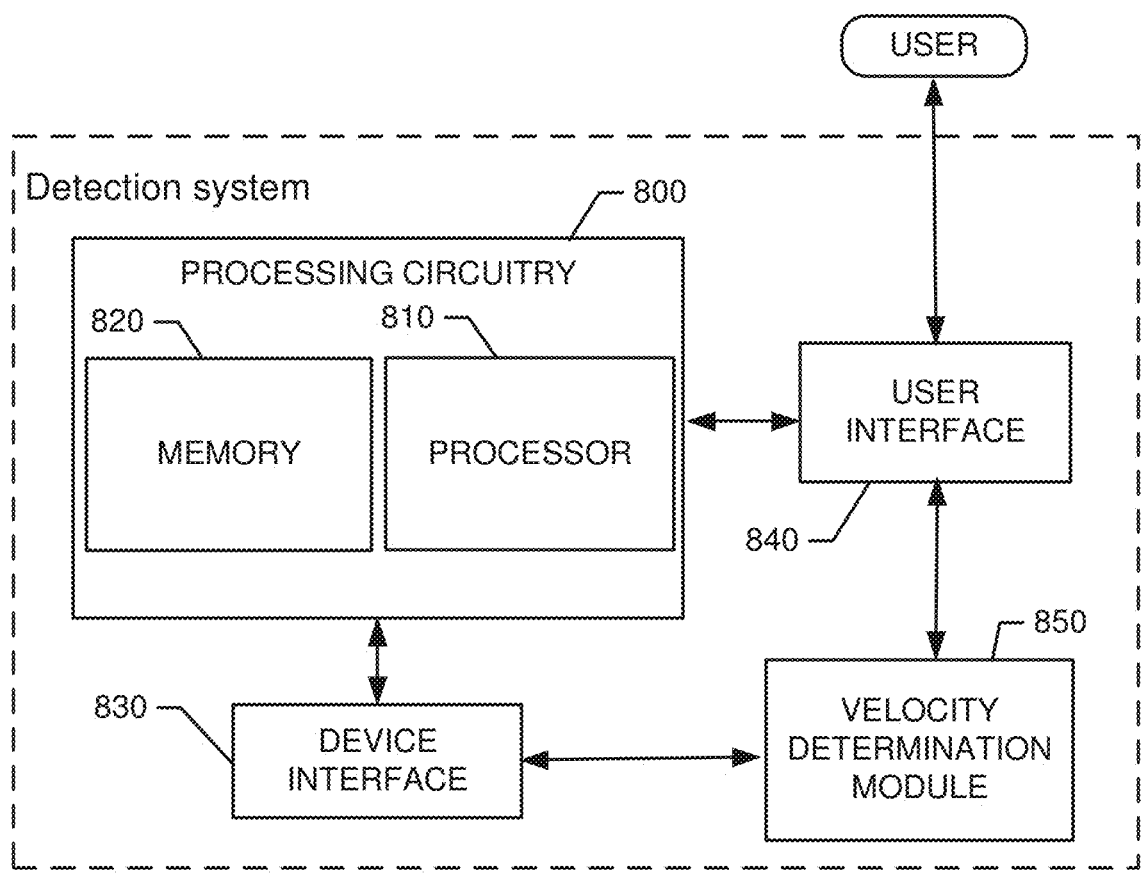
FIG. 8 illustrates a block diagram of a detection system according to an example embodiment.

FIG. 8 illustrates a block diagram of a detector or detection system in greater detail in accordance with an example embodiment. Referring now to FIG. 8, a detector or detection system may include or otherwise be in communication with processing circuitry 800 that is configurable to perform actions in accordance with example embodiments described herein. As such, for example, at least some of the functions attributable to the image data processor 810 may be carried out by or otherwise instructed by the processing circuitry 800. The processing circuitry 800 may therefore provide the hardware for hosting software to configure the system for analysis techniques consistent with example embodiments. Detection of velocity information using processes that employ LDV principles and the structures described herein may then be accomplished using the processing circuitry 800.

The processing circuitry 800 may be configured to perform data processing, control function execution and/or other processing and management services according to an example embodiment of the present invention. In some embodiments, the processing circuitry 800 may be embodied as a chip or chip set. In other words, the processing circuitry 800 may comprise one or more physical packages (e.g., chips) including materials, components and/or wires on a structural assembly (e.g., a baseboard).

In an example embodiment, the processing circuitry 800 may include one or more instances of a processor 810 and memory 820 that may be in communication with or otherwise control a device interface 830 and, in some cases, a user interface 840. As such, the processing circuitry 800 may be embodied as one or more instances of a circuit chip (e.g., an integrated circuit chip) configured (e.g., with hardware, software or a combination of hardware and software) to perform operations described herein.

The user interface 840 (if implemented) may be in communication with the processing circuitry 800 to receive an indication of a user input at the user interface 840 and/or to provide an audible, visual, mechanical or other output to the user. As such, the user interface 840 may include, for example, a display, printer, one or more buttons or keys (e.g., function buttons), and/or other input/output mechanisms (e.g., keyboard, touch screen, mouse, microphone, speakers, cursor, joystick, lights and/or the like). The user interface 840 may display information indicating a velocity measurement or certain characteristics of a data set (e.g., including velocity information or other characteristics related thereto) being processed by the detector or detection signal. The velocity measurement or characteristics of the data set may then be processed and information associated therewith may be presented on a display of the user interface 840 based on instructions executed by the processing circuitry 800 for the analysis of the data according to prescribed methodologies and/or algorithms. Moreover, in some cases, the user interface 840 may include options for selection of one or more reports or displays to be generated based on the analysis of a given data set.

The device interface 830 may include one or more interface mechanisms for enabling communication with other external devices (e.g., output devices, input devices and/or the like) or internal functional components of the detection system. In some cases, the device interface 830 may be any means such as a device or circuitry embodied in either hardware, or a combination of hardware and software that is configured to receive and/or transmit data from/to devices in communication with the processing circuitry 800.

In an exemplary embodiment, the memory 820 may include one or more non-transitory memory devices such as, for example, volatile and/or non-volatile memory that may be either fixed or removable. The memory 820 may be configured to store information, data, applications, instructions or the like for enabling the detector or detection system to carry out various functions in accordance with example embodiments of the present invention. For example, the memory 820 could be configured to buffer input data for processing by the processor 810. Additionally or alternatively, the memory 820 could be configured to store instructions for execution by the processor 810. As yet another alternative or additional feature, the memory 820 may include one or more databases that may store a variety of data sets indicative of patterns that are configured to trigger specific responses or algorithms, image data processing techniques, processing algorithms and/or the like to be employed for the execution of example embodiments. Among the contents of the memory 820, applications may be stored for execution by the processor 810 in order to carry out the functionality associated with each respective application. In some cases, the applications may include directions for control of the detector or detection system to process data received. In particular, in some cases, the applications may include instructions for directing operation of a velocity determination module 850 relative to sets of data that may each correlate to a single depth (if one focus point/detector is used) or multiple depths (if multiple focus points/detectors are used, as shown in FIG. 7). In some cases, the applications may further include directions for generating an output as one or more reports, displays or other outputs of data or analytical work product associated with analysis of the sets of data as described herein.

The processor 810 may be embodied in a number of different ways. For example, the processor 810 may be embodied as various processing means such as one or more of a microprocessor or other processing element, a coprocessor, a controller or various other computing or processing devices including integrated circuits such as, for example, an ASIC (application specific integrated circuit), an FPGA (field programmable gate array), or the like. In an example embodiment, the processor 810 may be configured to execute instructions stored in the memory 820 or otherwise accessible to the processor 810. As such, whether configured by hardware or by a combination of hardware and software, the processor 810 may represent an entity (e.g., physically embodied in circuitry—in the form of processing circuitry 800) capable of performing operations according to embodiments of the present invention while configured accordingly. Thus, for example, when the processor 810 is embodied as an ASIC, FPGA or the like, the processor 810 may be specifically configured hardware for conducting the operations described herein. Alternatively, as another example, when the processor 810 is embodied as an executor of software instructions, the instructions may specifically configure the processor 810 to perform the operations described herein.

In an example embodiment, the processor 810 (or the processing circuitry 800) may be embodied as, include or otherwise control the detector or detection system. As such, in some embodiments, the processor 810 (or the processing circuitry 800) may be said to cause each of the operations described in connection with the detector or detection system by directing the detector or detection system to undertake the corresponding functionalities responsive to execution of instructions or algorithms configuring the processor 810 (or processing circuitry 800) accordingly.

The velocity determination module 850 may be configured to process data received from the detector or detection system separately for each discrete focus point (if more than one exists), which is correlated with a corresponding depth.

Thus, range data may be separately processed (in parallel or series) in order to generate respective different data sets corresponding to each respective depth. The processing techniques employed may be similar to those described above. In this regard, the velocity determination module 850 may employ the principles of operation of Doppler velocimeters to determine particle velocity with further knowledge of the unique structure employed for example embodiments. As such, for example, the photodetector may generate an electrical signal proportional to the Doppler shift detected responsive to receipt of the first and second beams, and provide data for analysis to the velocity determination module 850. The velocity determination module 850 may then determine the particle velocity based on knowing the angular separation between the beams when they arrive at the photodetector. However, additional processing may also be included.

Figure 9:
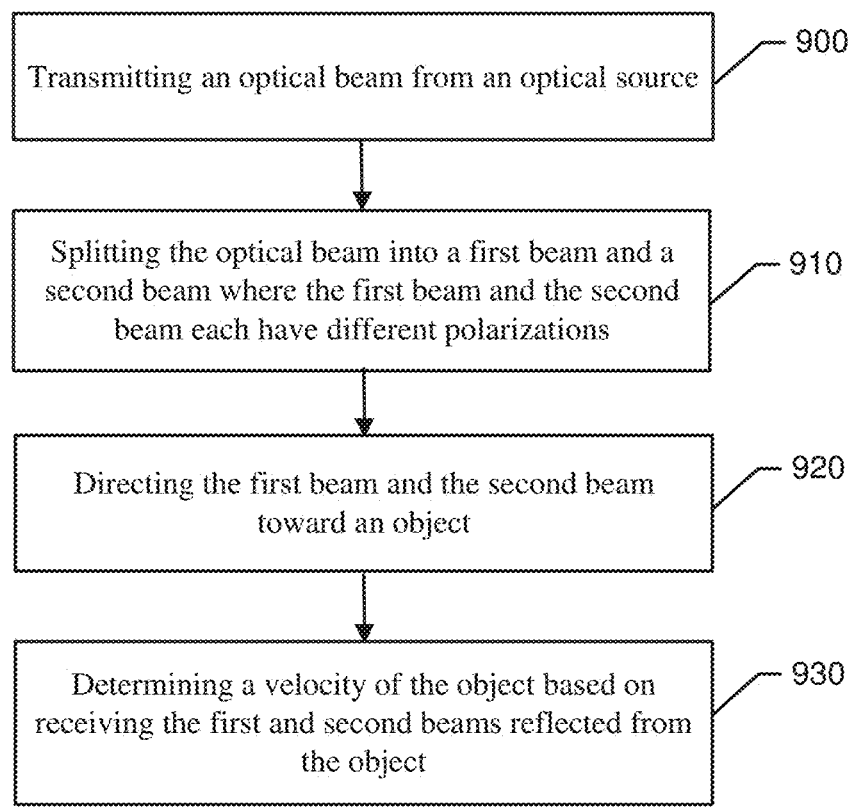
FIG. 9 shows an exemplary block diagram of a method according to an example embodiment.

FIG. 9 is a flowchart of a method and program product according to an example embodiment of the invention. In this regard, a method for particle velocity measurement may include transmitting an optical beam from an optical source at operation 900, splitting the optical beam into a first beam and a second beam where the first beam and the second beam each have different polarizations at operation 910, directing the first beam and the second beam toward an object at operation 920, and determining a velocity of the object based on receiving the first and second beams reflected from the object at operation 930.

In some embodiments, additional optional operations may be included or the operations described above may be modified or augmented. Each of the additional operations, modification or augmentations may be practiced in combination with the operations above and/or in combination with each other. Thus, some, all or none of the additional operations, modification or augmentations may be utilized in some embodiments. In an example embodiment, splitting the optical beam may include splitting the first beam and the second beam such that the first and second beams are separated from each other by a small angle (e.g., <5 degrees) by the beam splitter before the respective beams encounter a medium associated with the object. In some cases, the method may further include horizontally polarizing the first beam and vertically polarizing the second beam before the object is encountered. In some examples, a 45 degree polarizer may be provided between the object and the detector. In an example embodiment, transmitting the optical beam from the optical source may include providing the first beam and the second beam such that they overlap each other until a medium associated with the object is encountered. In some examples, the first beam may be polarized horizontally and the second beam may be polarized vertically after the object is encountered. In an example embodiment, the method may further include providing a lens disposed between the beam splitter and the detector. In such an example, a 45 degree polarizer may be provided between the lens and the detector. In some embodiments, providing the lens may include defining a plurality of focus points, and a separate instance of the detector may be disposed at each of the plurality of focus points (e.g., multiple respective detectors may be positioned with one at each focus point). In some examples, each of the focus points may correspond to a different depth within the object to measure velocity of particles at corresponding different depths. In an example embodiment, the method may further include measuring Doppler shift, and the Doppler shift measurement may be scaled based on an angle between the first beam and the second beam due to the reduction of Doppler shift experienced based on the angle. As such, the Doppler shift measured for each respective angle is known to be less than the actual Doppler shift based on the amount of the angle. By knowing the angle, the Doppler shift measurements can be scaled up to determine the actual Doppler shift from the measured Doppler shift.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe exemplary embodiments in the context of certain exemplary combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. In cases where advantages, benefits or solutions to problems are described herein, it should be appreciated that such advantages, benefits and/or solutions may be applicable to some example embodiments, but not necessarily all example embodiments. Thus, any advantages, benefits or solutions described herein should not be thought of as being critical, required or essential to all embodiments or to that which is claimed herein. Although specific terms are employed herein, they are used in a generic and descriptive sense only and not for purposes of limitation.

That which is claimed:

1. A particle velocity measurement system comprising:
an optical source configured to generate an optical beam;
a beam splitter configured to split the optical beam into a first beam and a second beam, the first beam and the second beam each having different polarizations;
a combiner configured to direct the first and second beams toward an object, wherein the first and second beams partially overlap to form a measurement volume; and
a plurality of detectors, each detector being disposed at a respective focus point along a common optical axis, each detector configured to receive the first beam and the second beam reflected from the object as the object moves through the measurement volume and configured to determine a velocity of the object based on changes in the reflected first beam relative to changes in the reflected second beam.

2. The particle velocity measurement system of claim 1, wherein the first beam and the second beam are separated from each other by an angle of less than five degrees.

3. The particle velocity measurement system of claim 1, wherein the first beam is polarized horizontally and the second beam is polarized vertically before the object is encountered.

4. The particle velocity measurement system of claim 3, wherein a 45 degree polarizer is disposed between the object and the detectors.

5. The particle velocity measurement system of claim 1, wherein, after encountering the object, the first beam is polarized horizontally and the second beam is polarized vertically.

6. The particle velocity measurement system of claim 5, further comprising a lens disposed between the object and the detectors.

7. The particle velocity measurement system of claim 6, wherein a 45 degree polarizer is disposed between the lens and the detectors.

8. The particle velocity measurement system of claim 1, wherein each of the focus points corresponds to a different depth within the object to measure velocity of objects at corresponding different depths.

9. The particle velocity measurement system of claim 1, wherein the detectors comprise a photodetector configured to measure a Doppler shift in the first beam as reflected from the object relative to the first beam prior to reflection from the object, or in the second beam as reflected from the object relative to the second beam prior to reflection from the object.

10. The particle velocity measurement system of claim 9, further comprising processing circuitry operably coupled to the plurality of detectors, the processing circuitry being configured to scale a measurement of the Doppler shift based on an angle between the first beam and the second beam.

11. A method for particle velocity measurement, the method comprising:
    transmitting an optical beam from an optical source;
    splitting the optical beam into a first beam and a second beam, the first beam and the second beam each having different polarizations;
    directing the first beam and the second beam toward an object, wherein the first and second beams partially overlap to form a measurement volume; and
    determining a velocity of the object based on receiving the first and second beams reflected from the object as the object moves through the measurement volume, the velocity being determined based on changes in the reflected first beam relative to changes in the reflected second beam;
    wherein the method further comprises defining a plurality of focus points along a common optical axis, wherein a separate instance of a detector configured to receive the reflected first beam and the reflected second beam is disposed at each focus point of the plurality of focus points, and wherein each of the focus points corresponds to a different depth within the object for determining the velocity of the object at corresponding different depths within the object.

12. The method of claim 11, wherein splitting the optical beam comprises splitting the first beam and the second beam such that the first and second beams are separated from each other by an angle of less than five degrees.

13. The method of claim 12, further comprising horizontally polarizing the first beam and vertically polarizing the second beam before encountering the object.

14. The method of claim 11, wherein transmitting the optical beam from the optical source comprises horizontally polarizing the first beam and vertically polarizing the second beam after encountering the object.

15. The method of claim 14, further comprising disposing a lens between the beam splitter and the detectors, and disposing a 45 degree polarizer between the lens and the detectors.

16. The method of claim 11, wherein determining the velocity of the object comprises measuring a phase change between the first and second beams reflected from the object.

17. The method of claim 11, further comprising measuring Doppler shift in the first beam as reflected from the object relative to the first beam prior to reflection from the object, or in the second beam as reflected from the object relative to the second beam prior to reflection from the object; and
    scaling the Doppler shift measurement based on an angle between the first beam and the second beam.

18. A particle velocity measurement system comprising:
    an optical source configured to generate an optical beam;
    a beam splitter configured to split the optical beam into a first beam and a second beam, the first beam and the second beam each having different polarizations;
    a combiner configured to direct the first and second beams toward an object, wherein the first and second beams partially overlap to form a measurement volume; and
    a plurality of detectors, each detector being disposed at a respective focus point, each detector configured to receive the first beam and the second beam reflected from the object as the object moves through the measurement volume and configured to determine a velocity of the object based on changes in the reflected first beam relative to changes in the reflected second beam;
    wherein the first beam is polarized horizontally and the second beam is polarized vertically before the object is encountered by the first beam and the second beam; and
    wherein a 45 degree polarizer is disposed between the object and the plurality of detectors.

* * * * *